US008550976B2

(12) United States Patent
Criscione

(10) Patent No.: US 8,550,976 B2
(45) Date of Patent: Oct. 8, 2013

(54) IMPLANTABLE DRIVER WITH NON-INVASIVE TRANSMURAL POWERING DEVICE FOR CARDIAC ASSIST AND COMBINED ASSIST AND SUPPORT DEVICES

(75) Inventor: John C. Criscione, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 13/310,604

(22) Filed: Dec. 2, 2011

(65) Prior Publication Data

US 2012/0142996 A1 Jun. 7, 2012

Related U.S. Application Data

(60) Provisional application No. 61/419,544, filed on Dec. 3, 2010.

(51) Int. Cl.
*A61N 1/362* (2006.01)
(52) U.S. Cl.
USPC ................................. 600/16; 607/33; 607/61
(58) Field of Classification Search
USPC ........................ 600/16; 607/33, 61
See application file for complete search history.

(56) References Cited

U.S. PATENT DOCUMENTS

| 4,185,617 | A | * | 1/1980 | Hutchins ........................ 600/16 |
| 5,089,017 | A | * | 2/1992 | Young et al. ................. 623/3.11 |
| 5,348,528 | A | * | 9/1994 | Vince .............................. 600/16 |
| 6,723,039 | B2 | | 4/2004 | French et al. |
| 2005/0187425 | A1 | | 8/2005 | Alferness et al. |
| 2006/0287568 | A1 | | 12/2006 | Jassawalla et al. |
| 2007/0276444 | A1 | | 11/2007 | Gelbart et al. |

FOREIGN PATENT DOCUMENTS

WO 2012075460 6/2012

OTHER PUBLICATIONS

International Search Report for PCT/US2011/063178 dated Jun. 25, 2012.

\* cited by examiner

*Primary Examiner* — Christopher D Koharski
*Assistant Examiner* — Michael Carey
(74) *Attorney, Agent, or Firm* — Chainey P. Singleton; Edwin S. Flores; Chalker Flores, LLP

(57) ABSTRACT

The present invention an implantable, sub-cutaneous, bellows-like device with one plate proximal (or superficial) to the skin surface and the other plate distal (or deep) to the skin surface having a component of a pneumatic/hydraulic driver for an implantable medical device such as a cardiac assist, cardiac support, or combined cardiac assist and support device and inducible magnet material on the distal plate of the bellows that can be magnetically drawn towards the proximal plate by the action of a magnet outside the body to contract the bellows or pressurize the fluid in the bellows.

23 Claims, 10 Drawing Sheets

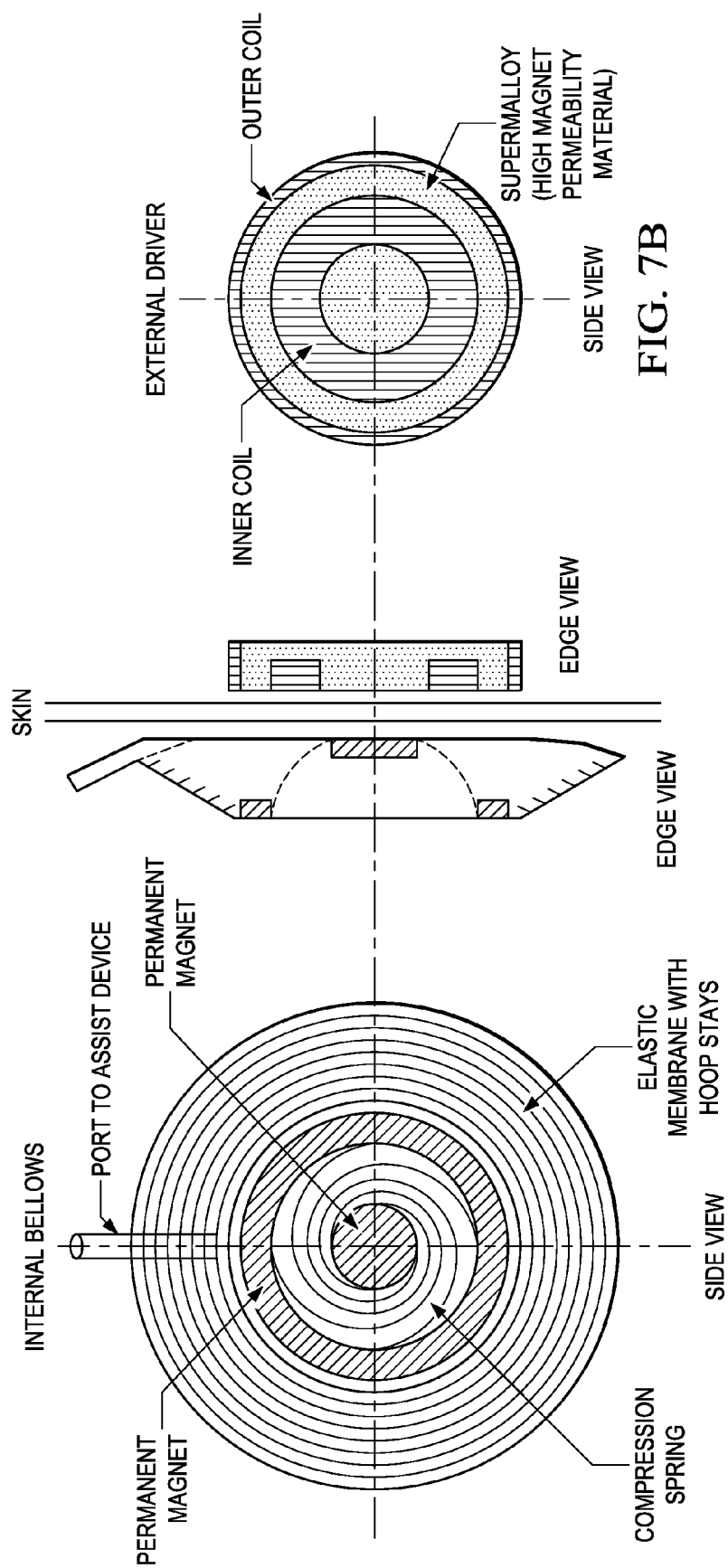

IMPLANTABLE DRIVER WITH NON-INVASIVE TRANSMURAL POWERING DEVICE FOR CARDIAC ASSIST AND COMBINED ASSIST AND SUPPORT DEVICES

CROSS-REFERENCE TO RELATED APPLICATIONS

This application claims priority to U.S. Provisional Application Ser. No. 61/419,544, filed Dec. 3, 2010, the entire contents of which are incorporated herein by reference.

TECHNICAL FIELD OF THE INVENTION

The present invention relates generally to medical devices and, more particularly, to implantable cardiac assist methods and implantable device drivers with non-invasive transdermal powering for cardiac assist or combined assist and support devices.

STATEMENT OF FEDERALLY FUNDED RESEARCH

Not Applicable.

SEQUENCE LISTING

Not Applicable.

INCORPORATION-BY-REFERENCE OF MATERIALS FILED ON COMPACT DISC

Not Applicable.

BACKGROUND OF THE INVENTION

Congestive Heart Failure (CHF) affects more than 5.3 million people in the U.S. with 550,000 new cases diagnosed each year. Incidence of CHF is increasing dramatically because of an aging population and improvement in treatments for heart attacks (age and surviving a heart attack are primary risk factors). CHF has an associated mortality rate of about 40% within 2 years of diagnosis; patients with the most advanced stages of CHF have a one-year mortality rate that exceeds 50%. For the 300,000 Americans in end-stage failure, transplant is the preferred treatment; however, with less than 3,000 hearts available this treatment plan is epidemiologically trivial. Hence cardiac assist and cardiac support devices are needed to help the heart meet baseline cardiac output requirements and potentially to reshape, regrow, and rehabilitate the heart. Many of these assist devices are electrically driven rotary type pumps; yet prior diaphragm displacement pumps, counter pulsation devices and direct cardiac compression devices require a pneumatic drive. Drivelines have conventionally been transcutaneous (crossing the skin barrier); but because of the increased risk of infection, there is a demand for drive systems that do not break the skin barrier. These are often called transcutaneous energy transfer systems because the energy is transferred using electromagnetic or sonic waves that do not disrupt the skin barrier.

BRIEF SUMMARY OF THE INVENTION

The present invention provides a magnetic bellows type device for powering and operating an implantable medical device having an external driver magnetic driver such as an electromagnet comprising an inner magnet or magnetic coils in a concentric arrangement with an outer magnet or magnetic coil, wherein the magnets or the magnetic coils are separated from each other by one or more layers of a magnetic force permeable material. The term bellows implies a device comprising a chamber that can be expanded or contracted by application of forces that pull (to expand) or push (to contract) opposing sides toward each other. To facilitate disclosure let the two opposing sides be referred to as plates. In this invention, the implanted bellows has its plates oriented along the surface of the skin with one plate deep below and the other superficial. One basic embodiment has a magnet or magnetically inducible material on the distal (or deep) plate. An extracorporeal (outside the body) magnetic type driver can thus pull the deep plate toward the proximal plate that is just below the skin surface. In so doing, the bellows will contract and inflate a device connected to the driver or pressurize the fluid in the bellows. Further embodiments include two separate yet combinable mechanisms to decrease the pressure on the skin when the pressurized fluid in the bellows pushes on the proximal plate of the bellows: 1) utilize a proximal plate that is significantly broader than the area of the plate exposed to bellows fluid, thus distributing the force over a larger area of skin, and 2) utilize permanent magnets on the proximal plate with an external magnetic device that repels the magnets, thus pushing the proximal plate away from the skin and reducing skin contact force. Further optional embodiments include the utilization of a bellows made of an elastomeric membrane comprising one or more hoop stays connecting the two plates of the bellows; and a port attached to the elastomeric membrane for communication between the internal driver bellows and the implantable medical device. The device may optionally include a heat shield or a convective cooling device placed on the external driver.

The present invention provides a magnetic bellows like device for powering and operating an implanted cardiac assist or combined assist and support device. Devices such as aortic counter pulsation devices and direct cardiac compression devices require generation of a pneumatic signal or pulse to drive the device in synchrony with the heart. The present invention is capable of so driving such devices and for driving the combined assist and support device of FIG. 1 with data in FIGS. 2-6.

BRIEF DESCRIPTION OF THE SEVERAL VIEWS OF THE DRAWINGS

For a more complete understanding of the features and advantages of the present invention, reference is now made to the detailed description of the invention along with the accompanying figures and in which:

FIG. 7A and FIG. 7B are images of the implantable driver with non-invasive powering illustrating the internal bellows (FIG. 7A) and external driver (FIG. 7B).

DETAILED DESCRIPTION OF THE INVENTION

Figure 1A:
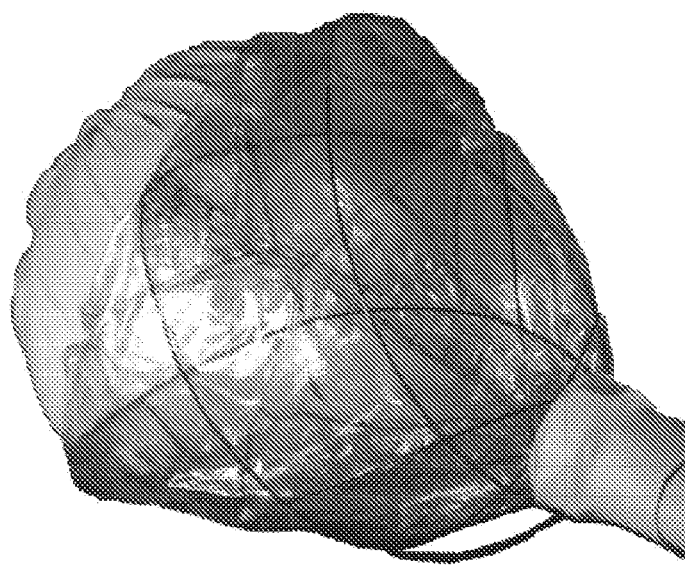
FIG. 1A is an image of a prototype of a cardiac combined assist and support device deployed about an excised ovine heart that is preserved and wrapped in thin latex for handling.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Support and Transmural Assist for Recovery. The present invention provides a non-invasive means of powering the invention discussed here. This represents a shift in the present paradigm wherein current device options are: non-adjustable cardiac support devices (CSDs) to constrain heart dilatation or blood pumps for circulatory assist. Specifically, the innovation is a minimally invasive device incorporating adjustable passive cardiac support and synchronous active cardiac assist—a biomedical device and technology designed to provide rehabilitative physical therapy for the heart muscle, mediating restorative remodeling processes to facilitate recovery of cardiac function. Moreover, this technology is less thrombogenic and more biocompatible than assist devices on the market because transmural (through the wall) assist is non-blood contacting. The present invention providing a therapeutic option targeting recovery of cardiac function is a substantial advancement in the treatment of heart failure and a great benefit to the healthcare economy, medical science, and society.

The present invention provides an innovative, fully implantable driver technology with non-invasive powering. The present invention provides a non-invasively charged implantable device, a bellows, to power the cardiac assist and support device (or any other implantable device requiring air pressure for operation), which is powered transdermally by the external driver.

Minimally invasive deployment and powering of implantable devices is preferred because associated trauma, recovery time, and costs are all decreased. These factors are amplified by heart failure because surgical survival depends on reduced trauma. The device and delivery system described herein is collapsible into a 1¼" diameter deployment tube and has been deployed into the pericardial sac using less invasive procedures. The present invention provides a device that buffers the heart with fluid filled sacs, thus isolating it from surrounding tissue and fibrous adhesions. The fluid sacs impart minimal impact on cardiac motion, and may be repeatedly adjusted by injection/evacuation of fluid into a subcutaneous port. An enlarged diseased heart can be gradually reduced in size via incremental adjustments to the passive support component of the device. The assist component of the present invention is non-blood contacting and thus does not bear some of the risks associated with current devices, i.e. blood pumps. The magnitude of assist can be graded and is synchronized with the heart function. The device can be turned off, thus making it non-obligatory. The versatile combination of support and assist provide the cardiologist with powerful therapeutic options to treat a wide variety of patient specific anomalies with the primary target, rehabilitation of the heart and recovery of cardiac function and performance. The present invention provides a medical device that provides heart assist and adjustable support that is minimally invasive, non-obligatory, non-blood contacting, and fully implantable with non-invasive transdermal powering.

There is strong evidence that cardiac support devices (CSDs) inhibit enlargement, while evidence suggesting restorative or rehabilitative remodeling is limited to case reports of "reverse remodeling" following treatment of an underlying disease or after placement of a left ventricular assist device in some patients awaiting transplant. Yet, contractile proteins are in a constant state of flux with absorption and formation occurring simultaneously—with rates equal to approximately half of the heart muscle mass per week. Essentially, the myocardium is continuously reconstituting itself by processes that are guided by physiologic demand and the local mechanical environment. With use of an adjustable cardiac support device to continually shrink the heart over a period of several months (with 3-4% reduction every 3 weeks), it is possible that heart size can be returned to normal—regardless of the etiology. Reduction of heart size is highly significant because size and function are related via Laplace's Law (i.e., wall stress is directly related to pressure and radius and inversely related to thickness). The mechanical advantage of reduced radius notwithstanding, a reduction is size is also likely to reduce the risk of arrhythmias, the primary cause of death for patients with end-stage heart failure.

The device of the present invention provides a fully implantable with non-invasive transdermal powering device that enables proactive intervention whereby specific mechanical conditions can be generated and employed to direct growth and remodeling events that are restorative and/or rehabilitative. As such an enlarged, dilated heart can be reduced in size by 30% over 6-8 mos. Additionally, the device has an active assist component that can increase stroke work as needed to maintain cardiac output, and provide a means for managing cardiogenic shock.

Combination of active and passive device: Though devices exist with specific indications for support, the proposed minimally invasive implantable device of the present invention provides the first device that has a dual component of active assist and passive support. Passive support is helpful long term, but causes acute increases in venous pressure. With the present invention, this complication can be mitigated.

Minimally invasive and minimal risk of infection and coagulation: The device of the present invention is a major advancement of heart assist technology that minimizes invasiveness, infection, and coagulation and most importantly this device allows customization of therapy based on the patient's response to the treatment strategy. Heart replacement is highly invasive and induces great trauma on the patient and complications from anti-rejection medication. The present technology incorporates design principles conducive to leading edge minimally invasive techniques.

Intra-aortic balloon pumps, or counterpulsation assist devices, are simple technologies inserted percutaneously that provide active circulatory assist. Because they touch the blood, they are more invasive than the technology proposed and have a limited ability to modulate heart motion and the end-diastolic (ED) and end-systolic (ES) configurations. They add motion to the heart by sucking on the vasculature or deflating during the heart's systolic contraction. The rebound of the arteries and circulatory demands, however, limit the ability of aortic balloon pumps to decrease the transmural pressure felt by the heart wall. Arterial pressure must remain a significant fraction of mean arterial pressure to maintain organ perfusion. In contrast, the device of the present invention modulates the transmural pressure gradient by raising the external pressure rather than lowering the internal blood pressure.

Advantage over LVAD's: For the left ventricular assist devices, there are multiple challenges in surgery, device operation and postoperative care due to the infection and coagulation risks associated with devices that touch blood. But over the last decade there have been supportive data towards destination therapy, and it is exciting that some patients in end-stage failure recovered completely when given a mechanical assist device while on the transplant waiting list. This demonstrates that heart recovery is possible. The device of the present invention is a great enhancement over blood pumps because it is implanted less invasively, assist can be stopped and started, there is no sewing to vessels or the heart, no contact with blood, and there is direct control of mechanical factors (ED and ES configurations) that are likely to be most important for recovery.

Of the passive ventricular restraints in clinical trials, Acorn's CorCap device is the leading device with a positive record of animal studies, clinical studies, and device sales in Europe. Regulatory approval in the US is less certain and a recent clinical trial was halted by FDA because an end point (increase in VO2 max) was not being met. The CorCap device can be implanted in a minimally invasive fashion, but it is limited in its ability to restore the heart to normal. Once inserted, it can limit the heart enlargement, but its size cannot be adjusted to continually reduce the ED configuration. To be most effective, the CorCap device needs to be implanted prior to end-stage failure. Deciding which patients need device intervention and which patients will recover on their own is difficult to determine in the early stages of failure. With the device of the present invention, intervention can be after the development of end-stage failure because ED can be continuously adjusted. In addition, passive devices have limited ability to modulate heart motion because they cannot supply pumping power. For example, the CorCap device cannot be undersized too much because it may limit heart filling and muscle stretch to the point that muscle contraction is too weak (i.e., an already shortened muscle cannot shorten much more). In contrast the present invention can supply systolic assist to normalize ejection while reducing the ED configuration. The present invention provides a device that also buffers the heart with fluid filled sacs thus allowing easy heart isolation in future surgeries.

The device of the present invention is an active and adjustable cardiac assist and support device with fully implantable driver internal bellows with non-invasive transdermal powering designed to enable the gradual reduction of EDV as a means to rehabilitate the heart muscle of patients with end-stage heart failure (systolic dysfunction). The device and deployment system are designed for less invasive implantation through a 1-2" sub-xiphoid incision in sheep (mini left thoracotomy in humans). The device is non-blood contacting, resides in the pericardial space and provides assist and support in a transmural (through the wall) manner, often called direct cardiac compression. Cardiac support capabilities are designed to be progressively actuated over a period of months, whereas assist capabilities are designed to temporarily restore cardiac output in the event of cardiogenic shock (e.g., likely post-cardiotomy). In addition, device refinements have been prototyped and tested in sheep, in an acute MI model, and in a model of cardiogenic shock (overdose of esmolol).

Important features of the device of the present invention include: the device of the present invention can be collapsed and inserted through a small incision, when the device of the present invention is depressurized it does not interfere with the heart, the support component can be progressively actuated to left-shift the end-diastolic pressure volume relationship, EDPVR, when pressurized during systole the device of the present invention morphs to end-systolic shape and thus assists the heart to change from ED configuration to ES configuration, pressurization of the device of the present invention does not dislodge the heart, and stroke work (SW) can be restored to normal in a shock model.

The device of the present invention takes on a rigid cup like shape (i.e., structurally supported cavity) when it is pressurized, and this naturally draws the heart into the device—such that suturing to the heart is not required. For example, it is very difficult to pull a water balloon out of a cup when they are placed inside of a bag with the air evacuated (i.e., like a closed chest). After air in the mediastinum is removed, the heart and device are pneumatically locked in a co-axial configuration. This feature was proven by fluoroscopy of device assist when pressurized. The air filled bladders are easily visible on flouro, and it is evident that the heart is not displaced by device activation, rather the heart diameter decreases when bladders inflate.

Figure 1B:
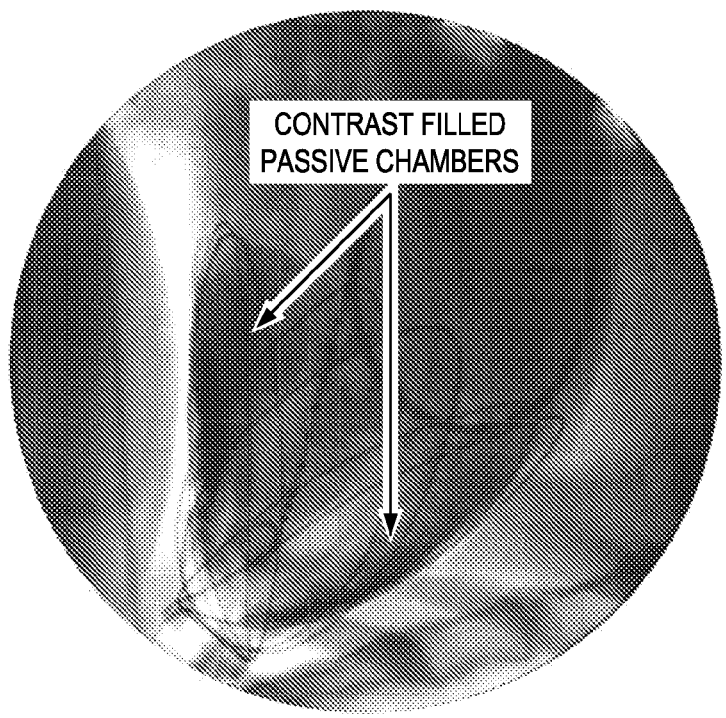
FIG. 1B is a fluoroscopic image of a fully deployed device with the passive support chambers inflated with saline.
Figure 1C:
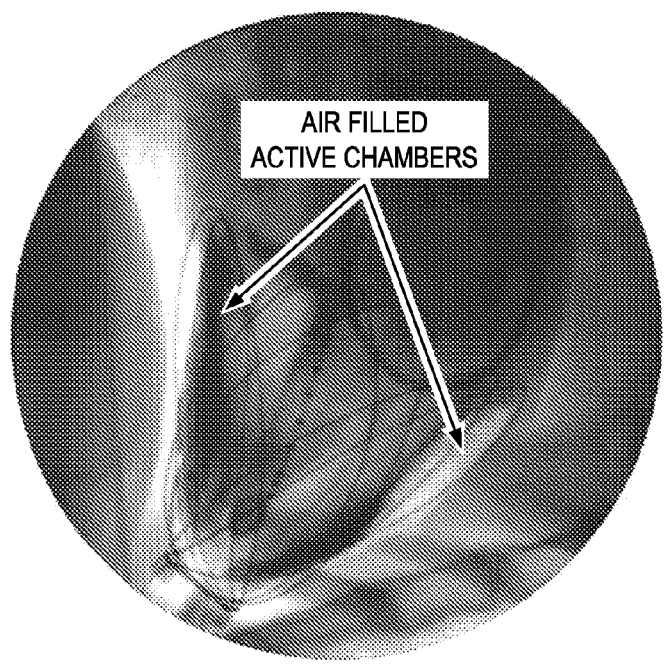
FIG. 1C is a fluoroscopic image of a fully deployed device with the active chambers partly inflated.

FIG. 1A is an image of a prototype of the device deployed about an excised ovine heart that is preserved and wrapped in thin latex for handling. The passive chambers are filled with contrast-saline solution for imaging. FIG. 1B is a fluoroscopic image of a fully deployed device showing the contrast-saline filled passive chambers. FIG. 1C is a fluoroscopic image of a fully deployed device with the active chambers partly inflated.

After multiple design iterations and testing of prototypes on a benchtop model of the ovine thorax, implantation was accomplished by using guide wires attached to a deployment tube containing the device. Fixed suture loops were sewn to the along the base of the device. The guide wires were then passed through the suture loops and the device was preloaded into the deployment tube. Once the guide wires were properly placed inside the pericardial space, the device could then be pushed out of the deployment tube and it would naturally follow the guide wires into the correct position. In order to get the guide wires placed properly, the tip of each wire was sutured together to form scoop or spoon shape. The scoop could then be easily inserted into the pericardial opening at which time the suture holding the guide wires together was released and the wires, made of nitinol, sprang into the correct position. The positioning of the guide wires was checked using fluoroscopy—the lateral boundaries of the heart are easily discernable, and a catheter in the coronary sinus indicates the lower boundary of the AV groove. With the guide wires positioned correctly the device was deployed out of the tube and along the guide wires. Once the device was fully deployed, the deployment tube and guide wires were removed from the pericardial space and the device implantation was complete. An image, using fluoroscopy, of the fully deployed device can be seen in FIGS. 1A, 1B, and 1C.

Using a Millar PV Catheter and the accompanying PVAN software (Millar Instruments Inc., Houston Tex.), device performance was evaluated. The present inventors have conducted ovine studies of the proposed assist/support device in which a PV loop catheter was used to determine the pressure-volume relationship. The PV relationships were determined for three cardiac states: normal, esmolol induced failure, and vena cava occlusion. High dose esmolol causes a significant reduction in contractility and is a reversible model of acute heart failure or cardiogenic shock. Vena cava occlusion was used to obtain the end-diastolic pressure volume relationship (EDPVR) to assess the ability of the device to modulate diastolic mechanics. Measures of heart rate (HR), maximum pressure (Pmax), minimum pressure (Pmin), maximum volume (Vmax), minimum volume (Vmin), end-diastolic pressure (Ped), end-diastolic volume (Ved), end-systolic pressure (Pes), end-systolic volume (Ves), stroke volume (SV), ejection fraction (EF), cardiac output (CO), and stroke work (SW) were obtained.

Figure 2A:
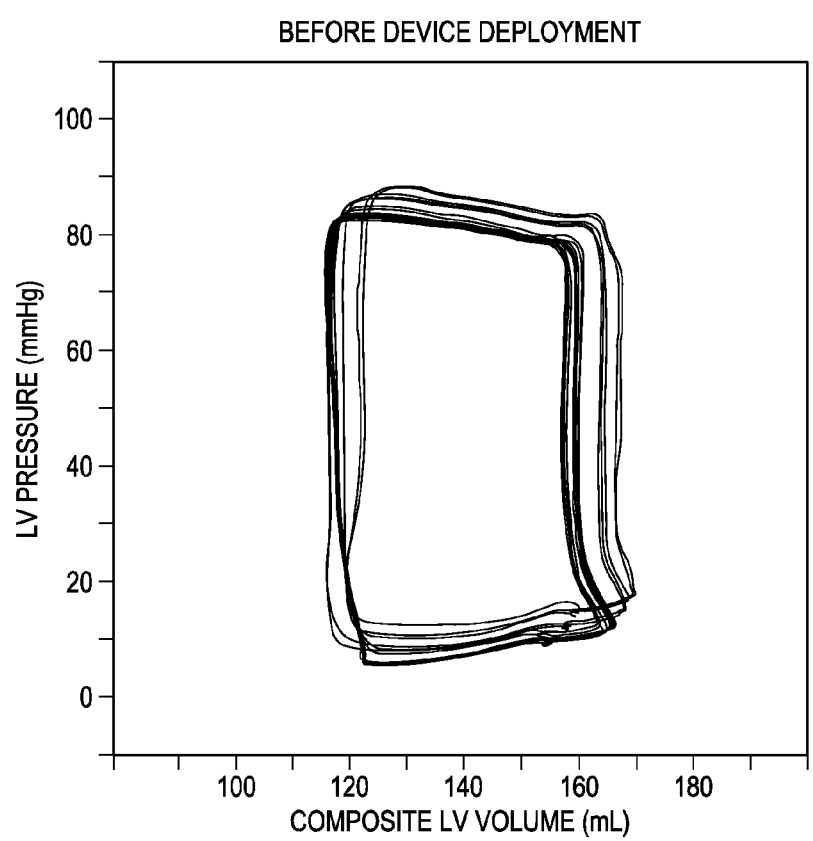
FIG. 2 is a plot of the pressure-volume loops of left ventricle prior to device implantation (FIG. 2A) and after device implantation (FIG. 2B) but before inflation of either the support or assist chambers.
FIG. 2C shows cardiac output (CO) and stroke work (SW), before and after deployment but before inflation of either the support or assist chambers.
Figure 2B:
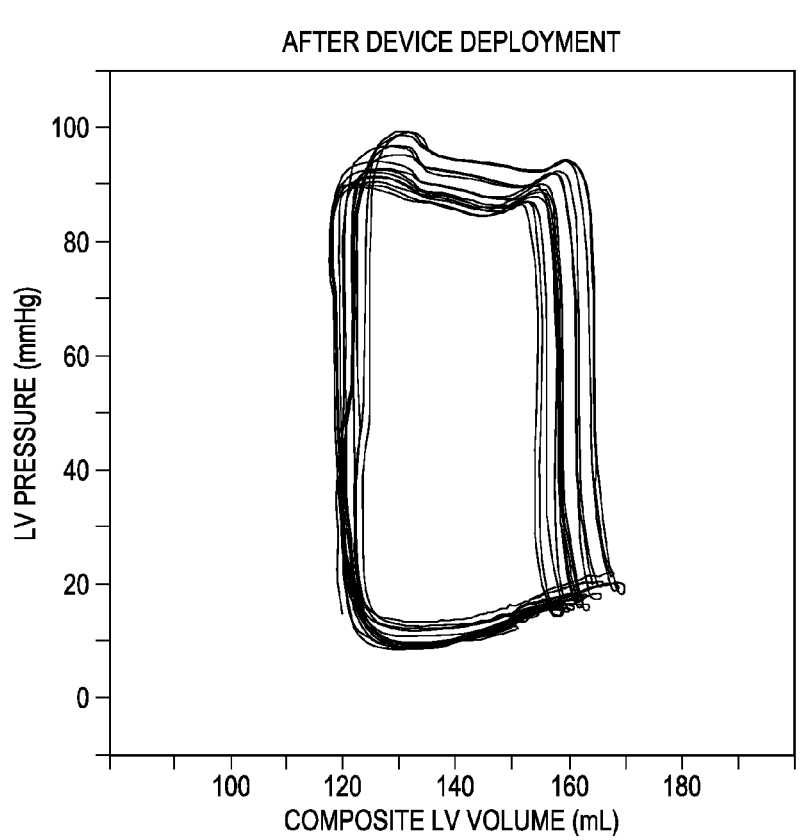
Figure 2C:
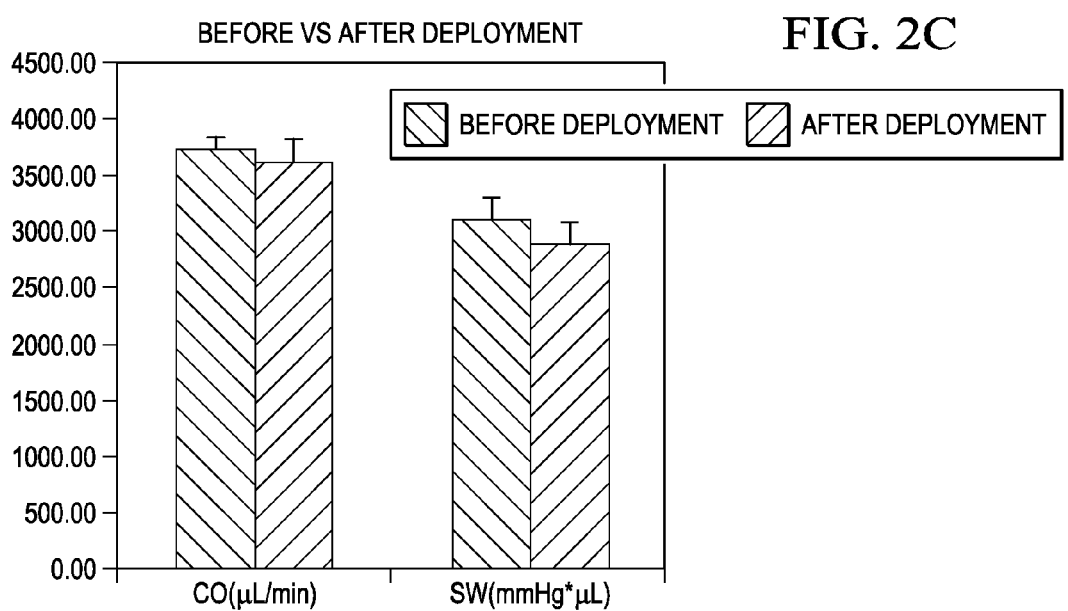

FIG. 2 is a plot of the pressure-volume loops of left ventricle prior to device implantation (FIG. 2A) and after device implantation (FIG. 2B) prior to inflation of either the support or assist chambers. Scales are the same; notice no significant change in the PV loops. FIG. 2C shows cardiac output (CO) and stroke work (SW), before and after deployment. Differences were not statistically significant. Error bars indicate the standard deviation. Implantation of the device did not significantly change cardiac function. When not pressurized, the device lacks rigidity and does not interfere with the heart performance. The PV loops before deployment did not change significantly after deployment. Stroke Volume (SV), Ejection Fraction (EF), Cardiac Output (CO), and Stroke Work (SW) were statistically similar. The heart rate did increase by approximately 10% after device implantation; however, the heart rate was still well within the normal range. FIG. 2 also provides a comparison of Cardiac Output (CO) and Stroke Work (SW) pre and post device deployment.

Figure 3A:
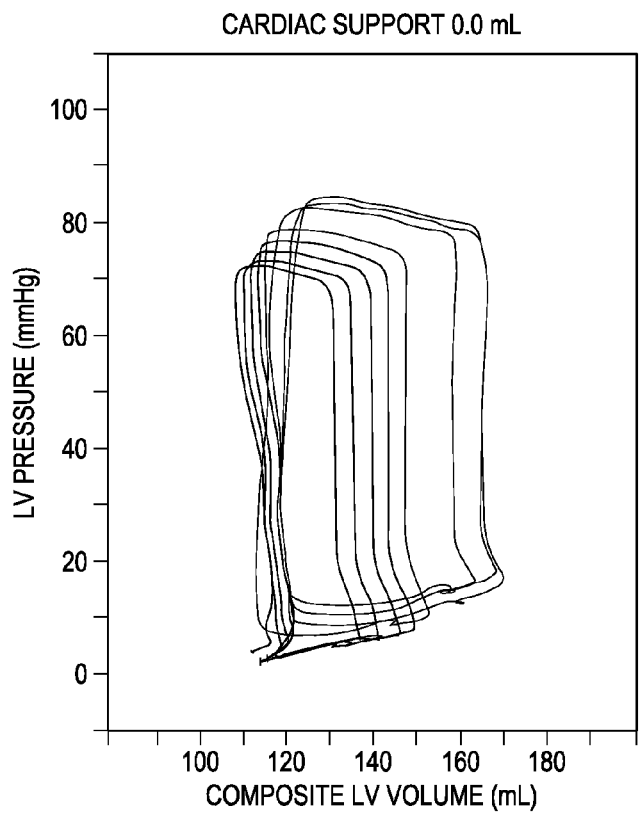
FIG. 3A is a graph of the PV loops of the left ventricle during vena cava occlusion in the absence of passive support, i.e. cardiac support of 0.0 ml.
Figure 3B:
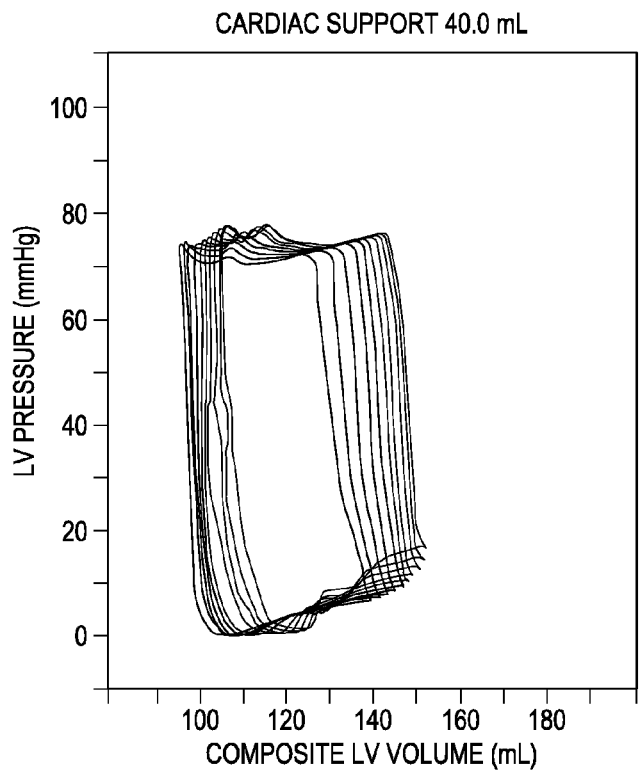
FIG. 3B is a graph of the PV loops of the left ventricle during vena cava occlusion with 40 mL of passive support.
Figure 3C:
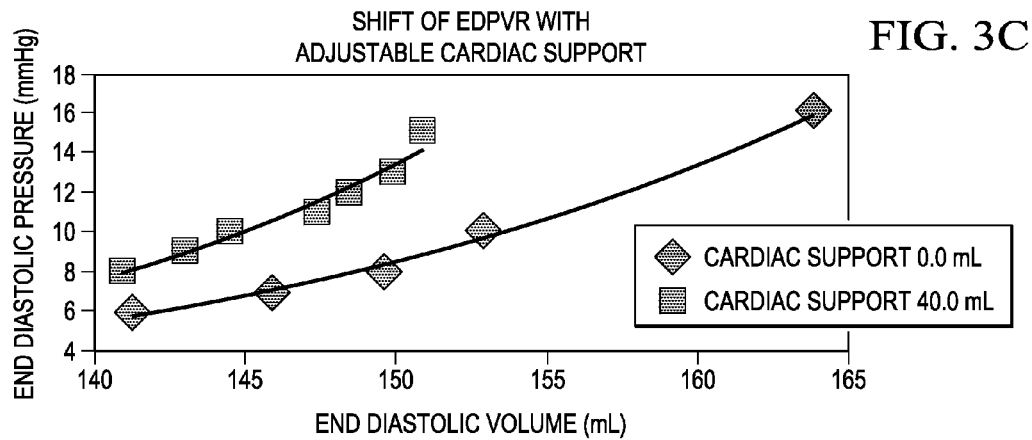
FIG. 3C is a graph of the end-diastolic pressure volume relationship (EDPVR) for both the 0 mL of support and 40 mL of support.

FIG. 3A is a graph of the PV loops of the left ventricle during vena cava occlusion in the absence of passive support, i.e. cardiac support of 0.0 ml. FIG. 3B is a graph of the PV loops of the left ventricle during vena cava occlusion with 40 mL of passive support. FIG. 3C is a graph of the EDPVR for both the 0 mL of support and 40 mL of support. Changes in the filling pressure of the left ventricle, known as preload, move the end-diastolic point, the lower right-hand corner of the PV loop. These points can often be approximated in a linear fashion and are collectively known as the end-diastolic pressure-volume relationship (EDPVR), which represents the passive filling mechanics of the left ventricle. The device's passive constraint/support component can alter the EDPVR in a positive manner, i.e., positive in the sense of shifting the EDPVR to the left because CHF progression shifts it to the right. The preload was altered by occluding the vena cava with a balloon. The vena cava occlusion was first done with the passive support chambers filled with 0 mL of saline to establish a baseline EDPVR. After the heart recovered, the vena cava was occluded again but this time the passive component of the CSD was filled with 40 mL of saline. The end-diastolic points for each PV loop are plotted in the bottom of FIG. 3C. The plots of the EDPVR for the 0 mL versus the 40 mL show that the EDPVR shifted leftward. This shift in the EDPVR indicates a decrease in the size of the left ventricle relative to filling pressure, i.e. the ventricle maintains the same filling pressure at a smaller volume. Therefore, the passive support is capable of modulating end-diastolic volume. When we substantially increase passive support and provide active assist, the EDPVR can be shifted further.

Figure 4A:
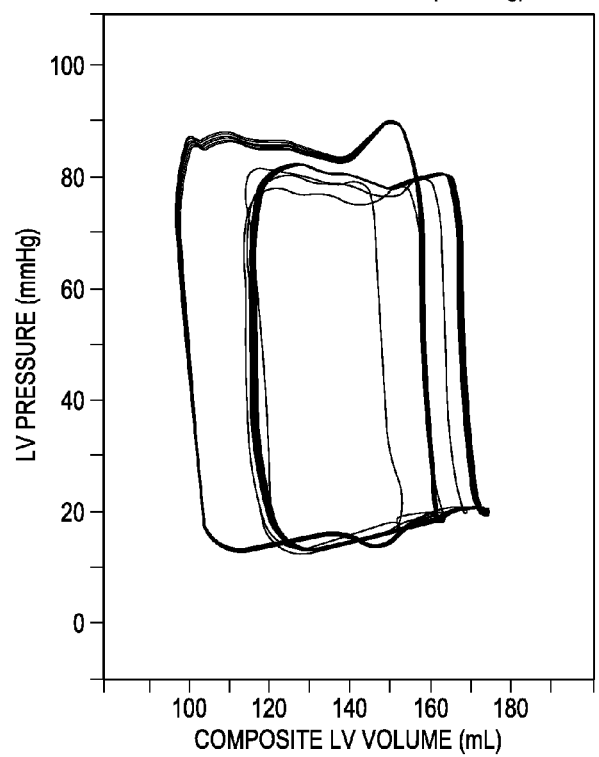
FIG. 4A is a graph of the PV loops of left ventricle for the normal cardiac state with 20 mm Hg active assist transitioned to 0 mm Hg active assist.
Figure 4B:
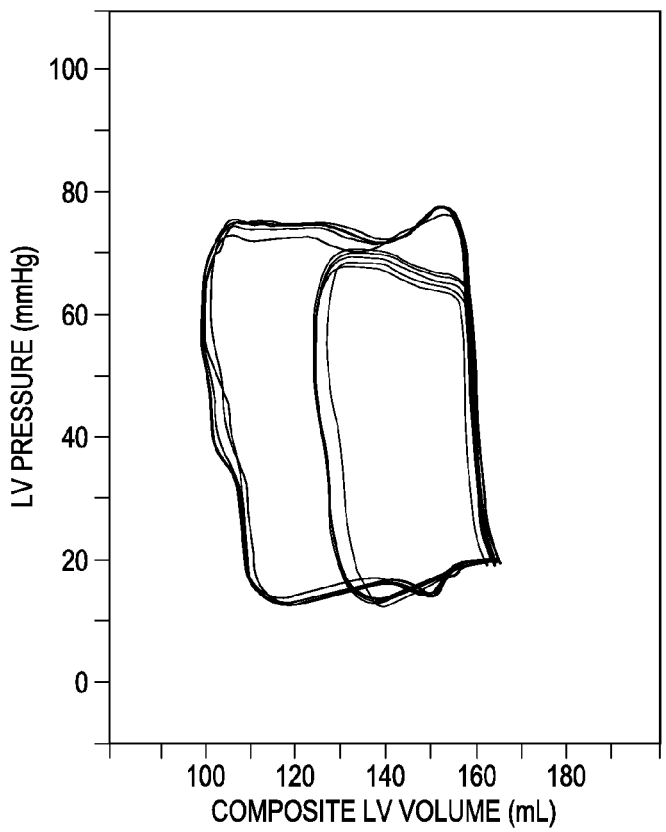
FIG. 4B is a graph of the PV loops of the left ventricle for the esmolol induced failure state with 20 mm Hg active assist transitioned to 0 mm Hg active assist.

FIG. 4A is a graph of the PV loops of the left ventricle for the normal cardiac state with 20 mm Hg active assist transitioned to 0 mm Hg active assist. FIG. 4B is a graph of the PV loops of the left ventricle for the esmolol induced failure state with 20 mm Hg active assist transitioned to 0 mm Hg active assist.

Figure 5A:
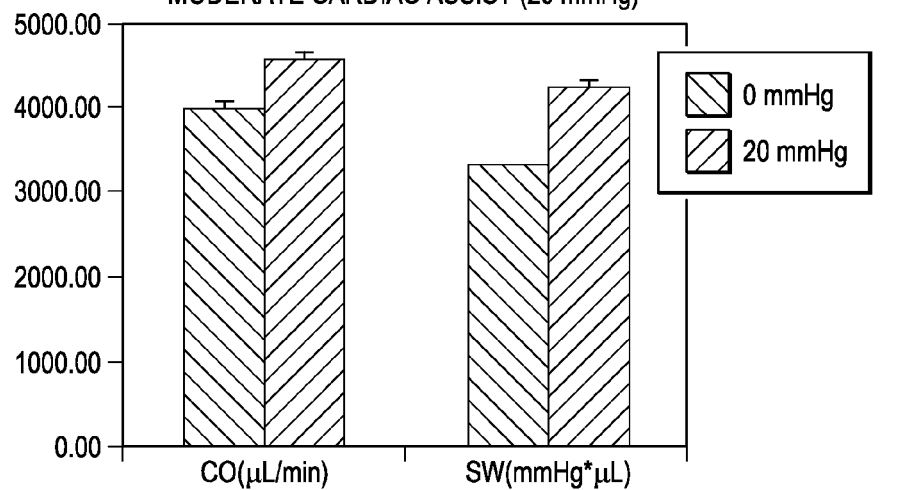
FIG. 5A left graph and 5B right graph are a side by side comparison of the cardiac output and stroke work for the normal cardiac and esmolol induced failure states with and without assist.

FIG. 5A left graph and 5B right graph are a side by side comparison of the cardiac output and stroke work for the normal cardiac and esmolol induced failure states with and without assist. Notice the drastic improvement in CO, and SW for the esmolol induced heart failure state when an active assist of 20 mm Hg is applied.

Figure 5B:
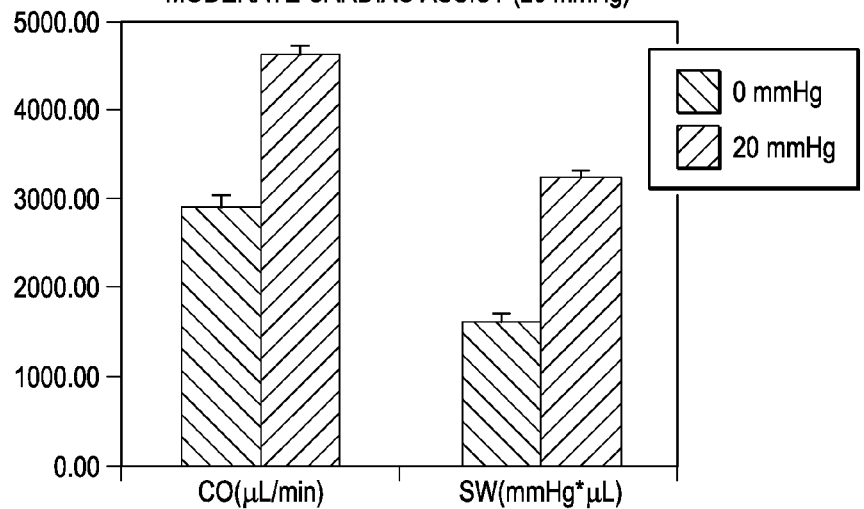

Normal Cardiac State with and without assist versus Esmolol Induced Failure with and without assist: For the normal cardiac and the esmolol induced failure states an active assist of 20 mm Hg was applied for approximately 5-10 cardiac cycles, after which the active assist was shut off for approximately 5-10 cardiac cycles. As expected, the 20 mm Hg active assist had a much more significant impact on the esmolol induced failure state. A comparison of the pressure-volume loops for both cases are in FIG. 4. Notice that the PV loops for both states have a larger area with the active assist of 20 mm Hg. The area within the PV loop is stroke work, and it increased dramatically in the esmolol induced failure state. FIG. 5 shows two critical measurements of cardiac performance for the normal cardiac state and esmolol induced heart failure state. For the normal cardiac state, an active assist of 20 mm Hg increased SV, EF, CO, and SW by 11.9%, 17.7%, 11.7%, and 20.5% respectively. For the esmolol induced heart failure state, high doses of esmolol infusion reduced SV by 30.7%, EF by 27.0%, CO by 29.3%, and SW by 49.9%. When the active assist of 20 mmHg was applied to the esmolol induced heart failure state SV, EF, CO, and SW increased by 37.9%, 38.2%, 58.8%, and 49.9%, respectively. The active assist of 20 mm Hg helped the esmolol failured heart to normalize the pressure-volume loops. In contrast, the active assist did little to change the PV loop of the normal heart—presumably because auto regulatory mechanisms kept the cardiac output constant at that which was needed to meet the physiological demand.

Figure 6A:
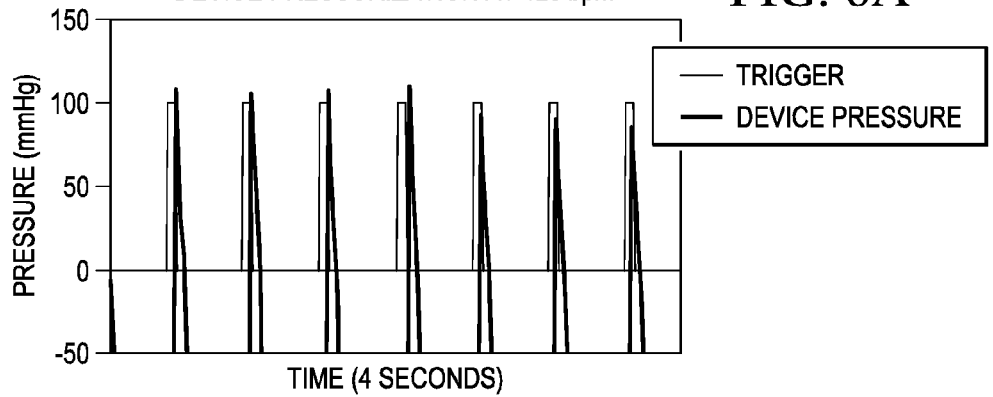
FIG. 6A is a graph at 120 BPM pressure in the device is reliably cycled in sync with the trigger.
Figure 6B:
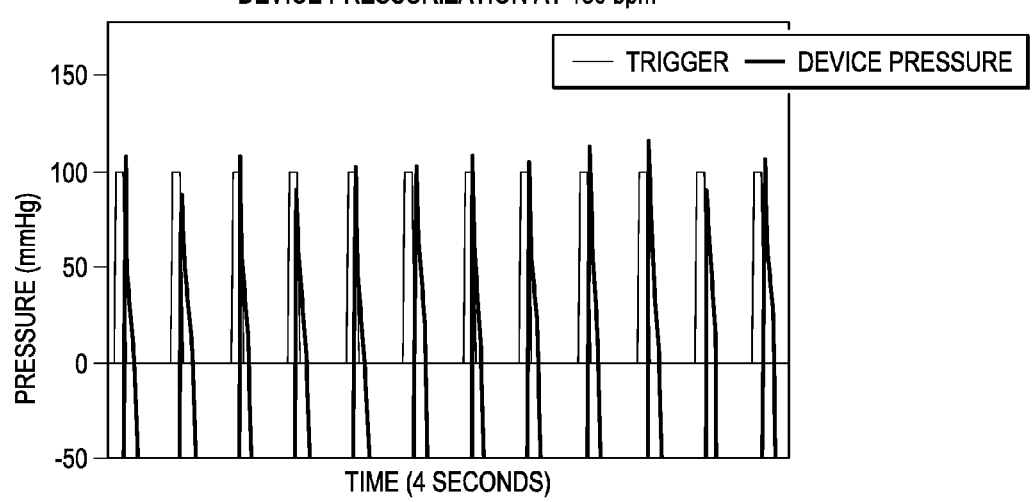
FIG. 6B is a graph at 180 BPM pressurization remains reliably synchronized with the trigger signal.
Figure 6C:
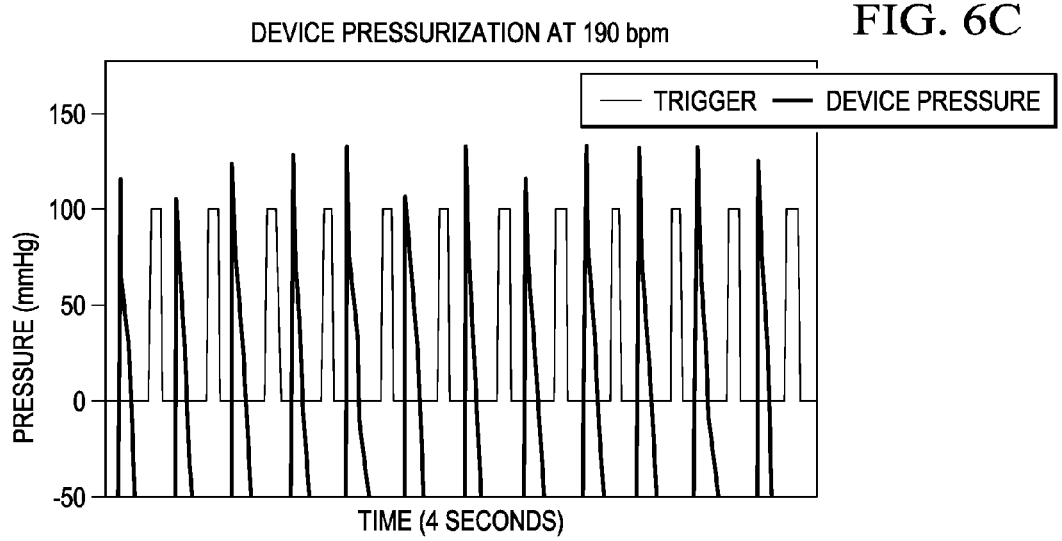
FIG. 6C is a graph at 190 BPM pressurization is no longer in sync.

FIG. 6A is a graph at 120 BPM pressure in the device is reliably cycled in sync with the trigger. Frequency was subsequently increased in 5 BPM intervals. FIG. 6B is a graph at 180 BPM pressurization remains reliably synchronized with the trigger signal. FIG. 6C is a graph at 190 BPM pressurization is no longer in sync with. This data places that the maximum operational frequency between 180-190 BPM, well above the maximum intended clinical use of the device (120 BPM). The present invention includes fatigue testing, ultimate pressurization, and ultimate frequency testing; we have converged on durable designs that exceed performance specifications.

In acute animal studies and benchtop tests, the device of the present invention has performed well. In prior studies, we have used a bedside pneumatic driver with a transcutaneous, pneumatic driveline. Although such drive technology is acceptable for use in intensive care units (i.e., as aortic balloon pumps are used), an implantable driver with non-invasive powering is needed for treating the large cohort of patients with end-stage heart failure.

Figure 7C:
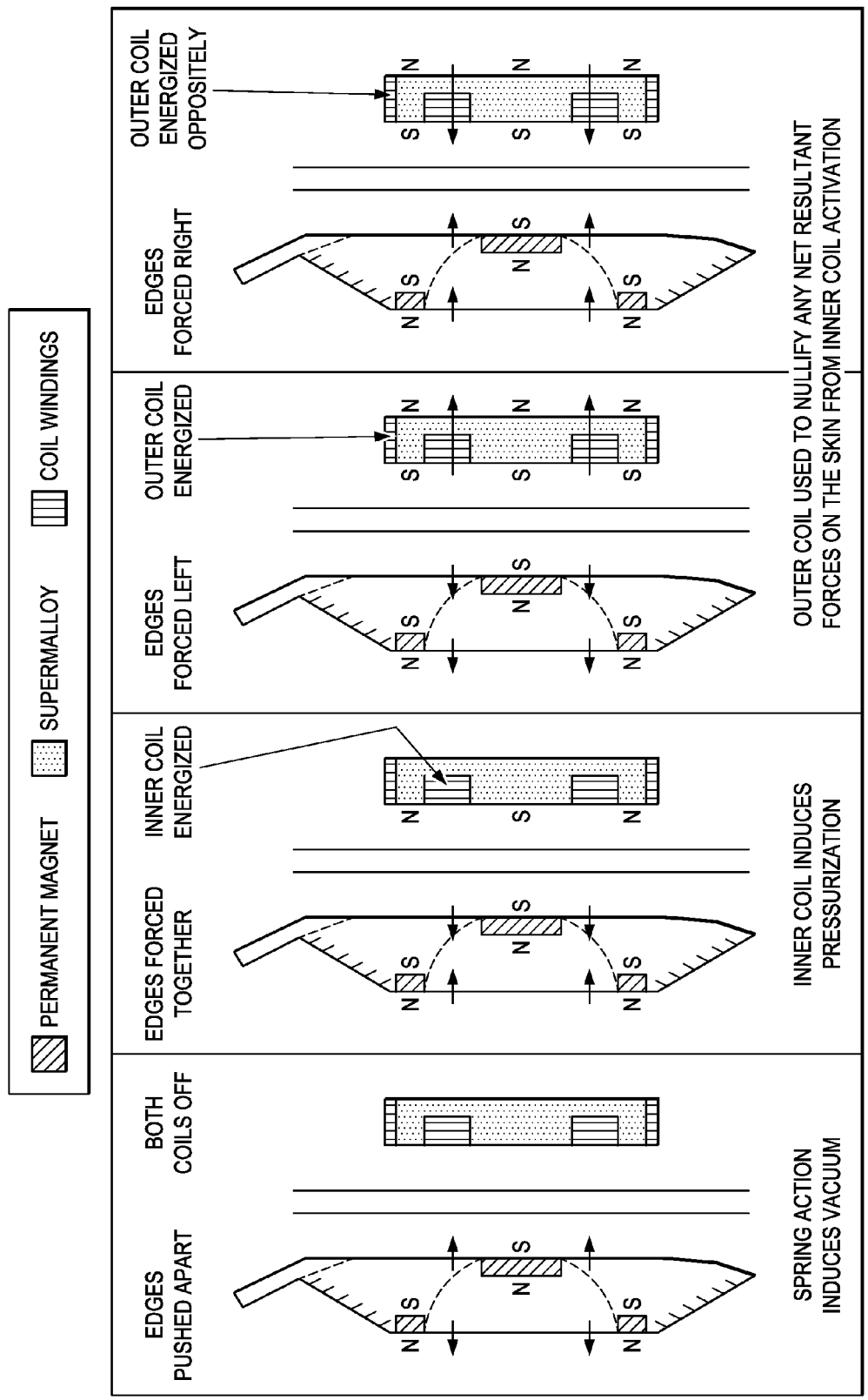
FIG. 7C is an image of the operation of the implantable driver with non-invasive powering illustrating the simultaneous operation of the internal bellows (FIG. 7A) with non-invasive powering and the external driver (FIG. 7B).

FIG. 7A and FIG. 7B are images of the implantable driver with non-invasive powering of the transmural assist illustrating the internal bellows (FIG. 7A) and external driver (FIG. 7B). FIG. 7C is an image of the operation of the implantable driver with non-invasive powering illustrating the internal bellows (FIG. 7A) with non-invasive powering of the transmural assist by the external driver (FIG. 7B).

With respect to an implantable driver with non-invasive powering, it is critical to note that transmural assist in the manner described above requires a driving gas at very low pressure (e.g., 20 mm Hg or 0.4 psi). The present invention provides in magnet technology to deliver adequate force (0.4 lbs per square inch), through the skin to a bellows below the skin. For example, a neodymium disk magnet (e.g., N52 grade, 1" diameter, ¼" thickness) can deliver force in the range of 5 lbs at a distance of 1 cm from a similar magnet. This is 10× greater force per area than what is needed.

Whereas prior transcutaneous energy transfer (TET) devices have used magnetic fields to induce electric currents in sub-dermal coils, the proposed driver uses magnetic fields to generate forces in sub-dermal permanent magnets. The difference is critical when considering the frequency of magnetic field oscillation. For TET devices capable of delivering enough power for heart assist (on the order of 1 W), the B field is oscillated at the low end of the radio frequency range (30 kHz); whereas for the proposed driver, the B field is oscillated in the range of heart rates (60 beats per minute or 1 Hz). Tissue heating is a major complication in the radio frequency range; however, tissue heating from 1 Hz B field oscillation is expected to be undetectable. The electromagnet may generate some heat, but heat conduction can be blocked with a heat shield and with convective cooling that has the intake (cool air) on the tissue side of the driver and outtake (warm air) on the back-end of the external part of the driver. The abdomen already moves to accommodate the action of an internal bellows (i.e., the lungs), so a periabdominal placement of the bellows is expected to be tolerated by patients.

The present invention uses magnetic modeling techniques to optimize magnet sizes and spacing to achieve appropriate forces and displacements for driving the device. The proposed driver shape is axis symmetric for simplicity of initial prototypes. The primary factor for driver performance is force generation (0.4 lbs per sq.in.) when the internal bellows is completely full (i.e., when the deepest magnet is farthest from the external driver) at the start of systole. However the force generation may be between 0.2-1.0 lbs per sq.in depending on the particular application. This parameter will limit the stroke length or displacement of the bellows. To assist the heart we need 150 ml of gas displacement (about 10 in3). A displacement of 1.5 cm is preferred to keep the sub dermal area at 75 cm2 (12 in2) which is roughly two bellows with a diameter of 3 in. In addition the pressure and displacement requirements (20 mm Hg and 150 ml) are consistent with that needed for a 300 ms stroke (systole is about 300 ms at 60 bpm).

The present invention also provides a direct cardiac compression device that promotes a contraction strain pattern on a diseased or damaged heart that reduces dyskinetic or hypokinetic motions.

Generally when a material is implanted in the body, the body recognizes the presence of the foreign material and triggers an immune defense system to eject and destroy the foreign material. This results in edema, inflammation of the surrounding tissue and biodegradation of the implanted material. As a result the biomedical implantable material must be carefully selected. Examples of suitable, biocompatible, biostable, implantable materials include but are not limited to polyetherurethane, polycarbonateurethane, silicone, polysiloxaneurethane, hydrogenated polystyrene-butadiene copolymer, ethylene-propylene and dicyclopentadiene terpolymer, and/or hydrogenated poly(styrene-butadiene) copolymer, poly(tetramethylene-ether glycol) urethanes, poly(hexamethylenecarbonate-ethylenecarbonate glycol) urethanes and combinations thereof. In addition, the present invention may be reinforced with filaments, made of a biocompatible, biostable, implantable polyamide, polyimide, polyester, polypropylene, polyurethane etc.

For example, at least a portion of the device may be made from elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated poly(styrene-butadiene) copolymer, poly(tetramethylene-ether glycol) urethanes, poly(hexamethylenecarbonate-ethylenecarbonate glycol) urethanes and combinations thereof.

The present invention also provides a method of reshaping the heart muscle of a patient by providing a cardiac compression device that compresses the heart during contraction without inverting or significantly perturbing the curvatures of the heart. A selectively contractible end-systolic heart shaped device is positioned about at least a portion of the periphery of the heart once access is made to the heart of the patient. The next step is the coupling of the driving source to the contractible end-systolic heart shaped device to contract and release during systole and diastole.

In one embodiment, the invention relates to a cardiac compression device that surrounds the heart and includes a shell and a compression mechanism. The compression mechanism is operable to actively promote a contraction strain pattern on a diseased or damaged myocardium that promotes beneficial growth and remodeling of the myocardium. More particularly, the contraction strain pattern may be characterized by non-inversion or lack of gross perturbation of the heart's curvature. In one embodiment the device has tapered compartments, e.g., end-systolic heart shape. The tapered compartments are connected to the compression source. Other configurations and multiple connections are also possible depending on the particular application and configuration.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An implantable, sub-cutaneous, bellows-like device with one plate proximal (or superficial) to the skin surface and the other plate distal (or deep) to the skin surface comprising:
   an implantable internal pneumatic/hydraulic driver for an implantable medical device such as a cardiac assist, cardiac support, or combined cardiac assist and support device wherein the implantable pneumatic/hydraulic internal driver comprises
   a distal plate comprising an inducible magnet material;
   a proximal plate separated from the distal plate by one or more bellows;
   a fluid within the one or more bellows; and
   a fluid connection to connect the implantable pneumatic/hydraulic internal driver to the implantable medical device wherein the distal plate can be magnetically drawn towards the proximal plate by the action of an external magnet outside the body to contract the bellows to pressurize the fluid in the bellows to allow the fluid to drive the implantable medical device.

2. The device of claim 1 with a proximal plate that is significantly larger than the distal plate; so that the pressure in the bellows is distributed over a larger skin area, thus reducing the pressure across the skin barrier.

3. The device of claim 1 with a spring type component between the distal and proximal plates to expand or depressurize the bellows.

4. The device of claim 2 with a spring type component between the distal and proximal plates to expand or depressurize the bellows.

5. The device of claim 1 with permanent magnets on the proximal plate to repel the proximal plate away from the skin to reduce the pressure on the skin that lies between the proximal plate and the magnet outside the body.

6. The device of claim 1, wherein the bellows is composed of: an elastomeric membrane with one or more hoop stays connecting the distal and proximal plates; and a port attached to the elastomeric membrane for communication between the internal driver and the implantable medical device.

7. An implantable, sub-cutaneous, bellows-like device with one plate proximal (or superficial) to the skin surface and the other plate distal (or deep) to the skin surface comprising:
   an implantable internal pneumatic/hydraulic driver for an implantable medical device such as a cardiac assist, cardiac support, or combined cardiac assist and support device wherein the implantable pneumatic/hydraulic internal driver comprises
   a distal plate comprising a permanent magnet material,
   a proximal plate separated from the distal plate by one or more bellows, and
   a fluid within the one or more bellows; and
   a fluid connection to connect the implantable pneumatic/hydraulic internal driver to the implantable medical device wherein the distal plate can be magnetically drawn towards or repelled away from the proximal plate by the action of a magnet outside the body, to contract (pressurize) or expand (depressurize) the bellows.

8. The device of claim 7 with a spring type component between the distal and proximal plates to enhance either the expansion or contraction of the bellows.

9. The device of claim 7 with a proximal plate that is significantly larger than the distal plate; so that the pressure in the bellows is distributed over a larger skin area, thus reducing the pressure across the skin barrier.

10. The device of claim 8 with a proximal plate that is significantly larger than the distal plate; so that the pressure in the bellows is distributed over a larger skin area, thus reducing the pressure across the skin barrier.

11. The device of claim 7 with permanent magnets on the proximal plate to repel the proximal plate away from the skin to reduce the pressure on the skin that lies between the proximal plate and the magnet outside the body.

12. The device of claim 7 wherein the bellows is composed of: an elastomeric membrane with one or more hoop stays connecting the distal and proximal plates; and a port attached to the elastomeric membrane for communication between the internal driver and the implantable medical device.

13. The device of claim 7, wherein the device may optionally comprise a heat shield or a convective cooling device placed on the external driver.

14. The device of claim 7, wherein the device comprises a sensor in communication with the internal driver.

15. The device of claim 7, wherein the device comprises a first sensor in communication with the internal driver and a second sensor in communication with a receiver.

16. The device of claim 12, wherein the elastomeric membrane has tapered compartments.

17. The device of claim 7, wherein the internal driver is in communication with a control circuitry configured to control the implantable medical device.

18. The device of claim 7, further comprising a device for monitoring one or more heart cycles to maintain coronary flow in the heart at a selected level.

19. The device of claim 7, further comprising a processing circuitry configured to determine a time of a myocardial relaxation and to provide a diastolic synchronization to synchrony in the respective times of myocardial relaxation.

20. The device of claim 7, further comprising a processing circuitry configured to maintain a coronary flow at a predetermined level and wherein the control circuitry changes one or more parameters dependent on the diastolic synchronization to maintain said coronary flow at the selected level.

21. A magnetic device for powering and operating an implanted cardiac assist or combined assist and support device comprising: an axis symmetric external driver comprising an inner magnet or magnetic coils in a concentric arrangement with an outer magnet or magnetic coil, wherein the magnets or the magnetic coils are separated from each other by one or more layers of a magnetic force permeable material; and an implantable axis symmetric internal driver comprising: a first magnet; a second magnet in a concentric arrangement with the first magnet, wherein the first magnet and the second magnet are separated by a compression spring; an elastomeric membrane in a concentric arrangement with the second magnet, wherein the elastomeric membrane comprises one or more hoop stays; and a port attached to the elastomeric membrane for communication between the internal driver and the cardiac assist or combined assist and support device.

22. A method of powering and operating an implanted cardiac assist or combined assist and support device comprising the steps of:
providing the implanted cardiac assist or combined assist and support device contoured to surround or be placed about the heart;
connecting a magnetic device for powering and operating the implanted cardiac assist or combined assist and support device, wherein the magnetic device comprises: an axis symmetric external driver comprising an inner magnet or magnetic coils in a concentric arrangement with an outer magnet or magnetic coil, wherein the magnets or the magnetic coils are separated from each other by one or more layers of a magnetic force permeable material; and an implantable axis symmetric internal driver comprising: a first magnet; a second magnet in a concentric arrangement with the first magnet, wherein the first magnet and the second magnet are separated by a compression spring; an elastomeric membrane in a concentric arrangement with the second magnet, wherein the elastomeric membrane comprises one or more hoop stays; and a port attached to the elastomeric membrane for communication between the internal driver and the cardiac assist or combined assist and support device; and
energizing the magnetic device to power and operate the implanted cardiac assist or combined assist and support device.

23. The method of claim 22, wherein the energization of the internal coil generates a magnetic field, wherein the magnetic field generates a force in the first and the second magnets of the internal driver to induce the pressurization of the assist or combined assist and support device.

* * * * *